(12) United States Patent
Csutak

(10) Patent No.: US 8,068,226 B2
(45) Date of Patent: Nov. 29, 2011

(54) METHODS AND APPARATUS FOR ESTIMATING A DOWNHOLE FLUID PROPERTY

(75) Inventor: Sebastian Csutak, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 284 days.

(21) Appl. No.: 12/014,918

(22) Filed: Jan. 16, 2008

(65) Prior Publication Data

US 2009/0180101 A1 Jul. 16, 2009

(51) Int. Cl.
*G01N 21/00* (2006.01)
(52) U.S. Cl. ...................................................... 356/432
(58) Field of Classification Search ........... 356/432–436
See application file for complete search history.

(56) References Cited

U.S. PATENT DOCUMENTS

| | | | |
|---|---|---|---|
| 5,303,775 | A | 4/1994 | Michaels et al. |
| 6,995,360 | B2 | 2/2006 | Jones et al. |
| 7,025,138 | B2 | 4/2006 | Kurkjian et al. |
| 7,490,664 | B2 * | 2/2009 | Skinner et al. ............... 166/57 |
| 2007/0081157 | A1 | 4/2007 | Csutak et al. |

OTHER PUBLICATIONS

Borri, S. et al., Frequency modulation spectroscopy by means of quantum-cascade lasers, Applied Physics B—Lasers and Optics, Jul. 7, 2006, pp. 223-229, 85 (2006), Springer-Verlang 2006.
Friedrich, A. et al., High-temperature (T=490 K) operation of 5.8 um quantum cascade lasers with InP/GaInAs waveguides, Electronics Letters, Oct. 28, 2004, vol. 40 No. 22, IEE 2004.
Hofstetter, Daniel et al., High-temperature operation of distributed feedback quantum-cascade lasers at 5.3 um, Applied Physics Letter, Jan. 23, 2001, pp. 396-398, vol. 78 No. 4, American Institute of Physics 2001.
Lee, Benjamin G. et al., Broadly Tunable Single-Mode Quantum Cascade Laser Source, 2007 Optical Society of America.
Lee et al, "Widely turnable single-mode quantum cascade laser source for mid-infrared spectroscopy," Appl. Phys. Lett., vol. 91 No. 23, Article 23101, Dec. 3, 2007, 3 pages.
Xie et al., "Nonlinear Optics with Quantum Cascade Lasers," Laser Physics, vol. 17, No. 5, pp. 672-679, May 2007, 8 pages.
International Searching Authority, International Search Report, International Application No. PCT/US 09/30893, mailing date Jul. 17, 2009, 3 pages.
International Searching Authority, Written Opinion, International Application No. PCT/US 09/30893, mailing date Jul. 17, 2009, 5 pages.

* cited by examiner

*Primary Examiner* — Michael P Stafira
(74) *Attorney, Agent, or Firm* — Cantor Colburn LLP

(57) ABSTRACT

Apparatus and method for estimating a downhole fluid property using a carrier conveyable into a well borehole, one or more light sources carried by the carrier, the one or more light sources comprising at least one quantum cascade laser light source, a fluid sample cell that receives light emitted from the one or more light sources, and at least one photodetector that detects light emitted from the one or more light sources after the light interacts with a fluid in the fluid sample cell.

17 Claims, 4 Drawing Sheets

METHODS AND APPARATUS FOR ESTIMATING A DOWNHOLE FLUID PROPERTY

CROSS-REFERENCE TO RELATED APPLICATIONS

Not Applicable

BACKGROUND

1. Technical Field

The present disclosure generally relates to well bore tools and in particular to apparatus and methods for downhole spectrometry.

2. Background Information

Oil and gas wells have been drilled at depths ranging from a few thousand feet to as deep as 5 miles. Wireline and drilling tools often incorporate various sensors, instruments and control devices in order to carry out any number of downhole operations. These operations may include formation testing, fluid analysis, and tool monitoring and control.

The environment in these wells present many challenges to maintain the tools used at depth due to vibration, harsh chemicals, and temperature. Temperature in downhole tool applications presents a unique problem to these tools. High downhole temperatures may reach as high as 200° C. (392° F.) or more, and sensitive electronic equipment may require cooling in order to operate properly in the downhole environment. An added problem is that space in the carrier assembly is usually limited to a few inches in diameter.

High resolution spectrometers, 1-2 nm bandpass for each optical channel for example, are typically completely located at a surface location with fluid samples being transported to the surface for analysis or they use optic fibers to carry light from the surface to a downhole sample. Some wireline tools use downhole spectrometers that analyze fluids in the downhole environment but generally at comparatively low spectral resolution of about 20-30 nm bandpass for each optical channel.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

Disclosed is an apparatus for estimating a downhole fluid property. The apparatus includes a carrier conveyable into a well borehole, one or more light sources carried by the carrier, the one or more light sources comprising at least one quantum cascade laser light source, a fluid sample cell that receives light emitted from the one or more light sources, and at least one photodetector that detects light emitted from the one or more light sources after the light interacts with a fluid in the fluid sample cell.

In another aspect, a method for estimating a downhole fluid property includes conveying one or more light sources into a well borehole using a carrier, the one or more light sources comprising at least one quantum cascade laser light source, emitting light from the at least one quantum cascade laser light source toward a fluid sample cell containing a downhole fluid, and detecting the light emitted from the at least one quantum cascade laser light source after the light interacts with the downhole fluid in the fluid sample cell using at least one photodetector.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF EXEMPLARY EMBODIMENTS

The present disclosure uses terms, the meaning of which terms will aid in providing an understanding of the discussion herein. As used herein, high temperature refers to a range of temperatures typically experienced in oil production well boreholes. For the purposes of the present disclosure, high temperature and downhole temperature include a range of temperatures from about 100° C. (212° F.) to about 200° C. (392° F.).

Figure 1:
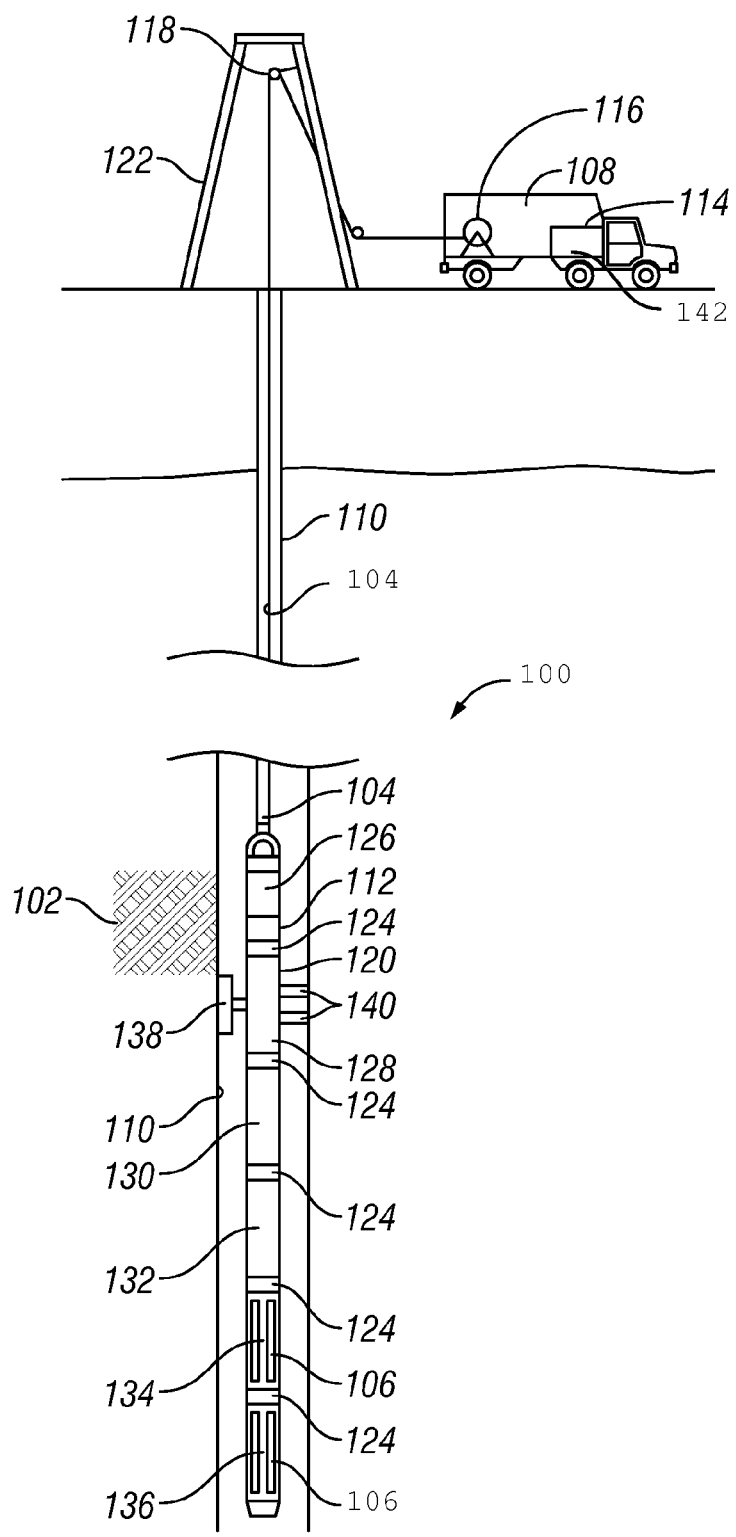
FIG. 1 is an exemplary wireline system according to several embodiments of the disclosure.

FIG. 1 schematically illustrates a non-limiting example of a wireline apparatus 100 according to several disclosed embodiments. In the example shown, a well borehole 110 traverses several subterranean formations 102. The well borehole 110 will typically be filled or at least partially filled with a fluid mixture which can include various gases, water, drilling fluid, and formation fluids that are indigenous to the subterranean formations penetrated by the well borehole. Such fluid mixtures are referred herein to as "well borehole fluids".

A formation evaluation tool 120 is conveyed in the well borehole 110 using a wire line 104. Wire line deployment and retrieval may be performed by a powered winch carried by a service truck 108, for example. The wireline 104 typically is an armored cable that carries data and power conductors for providing power to the formation evaluation tool 120 and to provide two-way data communication between a tool processor 112 and a controller 114 that may be carried by the service truck 108. The wireline 104 typically is carried from a spool 116 over a pulley 118 supported by a derrick 122. The spool 116 may be carried by the truck 108 as shown for on-land operations, by an offshore rig for underwater operations, or by any other suitable mobile or fixed supporting structure. The controller 114 may include a processor 142, such as within a computer or a microprocessor, data storage devices, such as solid state memory and magnetic tapes, peripherals, such as data input devices and display devices, and other circuitry for controlling and processing data received from the tool 120. The surface controller 114 may further include one or more computer programs embedded in a computer-readable medium accessible to the processor 142 in the controller 114 for executing instructions contained in the computer programs to perform the various methods and functions associated with the processing of the data from the tool 120. In several embodiments to be described in further detail later, the tool 120 includes a downhole spectrometer.

The lower portion of the formation evaluation tool 120 may include an assembly of several tool segments that are joined end-to-end by threaded sleeves or mutual compression unions 124. An assembly of tool segments suitable for the present invention may include a hydraulic, electrical, or electro-mechanical power unit 126 and a formation fluid extractor 128. A large displacement volume motor/pump unit 130 may be provided below the extractor 128 for line purging. A similar motor/pump unit 132 having a smaller displacement volume may be included in the tool in a suitable location, such as below the large volume pump, for quantitatively monitoring fluid received by the tool 120. One or more sample tank magazine sections (two are shown 134, 136) may be included for retaining fluid samples from the small volume pump 132. Each magazine section 134, 136 may have several fluid sample tanks 106.

The formation fluid extractor 128 may include an extensible suction probe 138 that is opposed by bore wall feet 140. Both, the suction probe 138 and the opposing feet 140 may be hydraulically or electro-mechanically extensible to firmly engage the well borehole wall. Construction and operational details of a suitable fluid extraction tool 128 are thoroughly described by U.S. Pat. No. 5,303,775, the specification of which is incorporated herein by reference.

Figure 2:
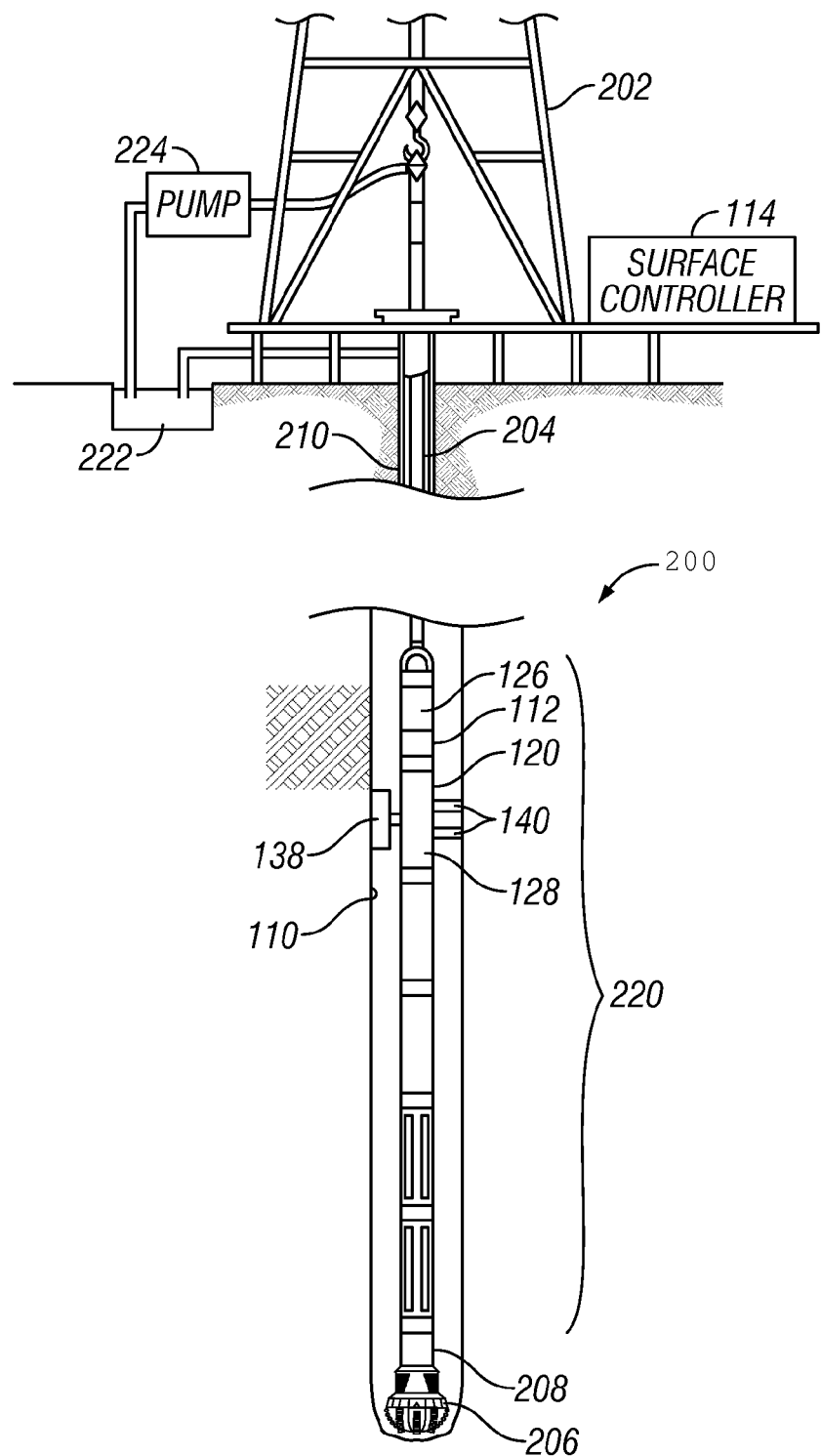
FIG. 2 illustrates a non-limiting example of a while-drilling system according to the disclosure.

FIG. 2 schematically illustrates a non-limiting example of a drilling system 200 in a measurement-while-drilling (MWD) arrangement according to one embodiment of the disclosure. A derrick 202 supports a drill string 204, which may be a coiled tube or drill pipe. The drill string 204 may carry a bottom hole assembly (BHA) 220 and a drill bit 206 at a distal end of the drill string 204 for drilling a borehole 210 through earth formations.

Drilling operations according to several embodiments may include pumping drilling fluid or "mud" from a mud pit 222, and using a circulation system 224, circulating the mud through an inner bore of the drill string 204. The mud exits the drill string 204 at the drill bit 206 and returns to the surface through an annular space between the drill string 204 and inner wall of the borehole 210. The drilling fluid is designed to provide the hydrostatic pressure that is greater than the formation pressure to avoid blowouts. The pressurized drilling fluid may further be used to drive a drilling motor 208 and may provide lubrication to various elements of the drill string 204.

In the non-limiting embodiment of FIG. 2, the BHA 220 may include a formation evaluation tool 120, a hydraulic, electrical, or electro-mechanical power unit 126, a tool processor 112 and a surface controller 114. The tool 120, power unit 126, the tool processor 112, and the controller 114 may be substantially similar to the like-numbered components described above and shown in FIG. 1. The while-drilling tool 120 may carry a fluid extractor 128 including a probe 138 and opposing feet 140. In several embodiments to be described in further detail later, the tool 120 includes a downhole spectrometer. The spectrometer may be used in either the while-drilling embodiments or in the wireline embodiments.

Those skilled in the art with the benefit of the present disclosure will recognize that the several embodiments disclosed are applicable to a formation fluid production facility without the need for further illustration. The several examples described below and shown in FIGS. 3-5 may be implemented using a wireline system as described above and shown in FIG. 1, may be implemented using a while-drilling system as described above and shown in FIG. 2 or may be implemented in a production facility to monitor production fluids.

Figure 3:
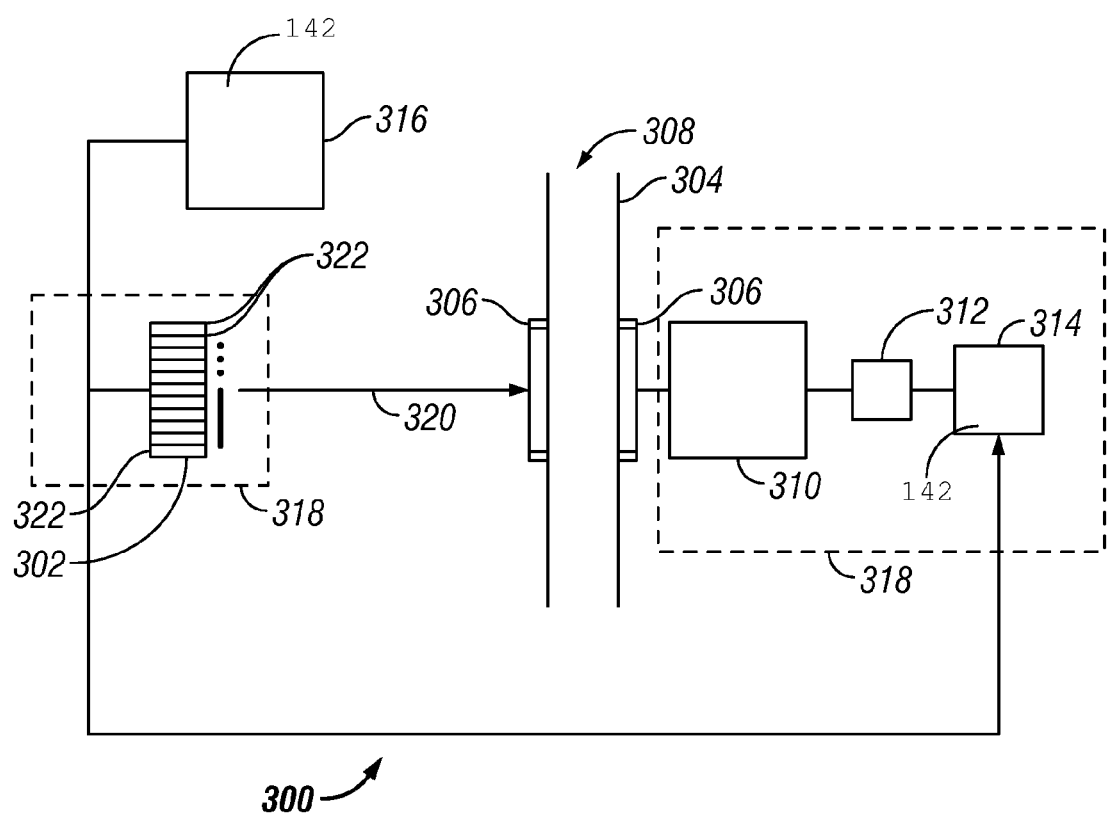
FIG. 3 is a non-limiting example of a downhole spectrometer that may be used with systems such as those depicted in FIGS. 1 and 2.

FIG. 3 schematically illustrates a non-limiting example of a downhole spectrometer 300 according to the disclosure. The downhole spectrometer 300 may be incorporated into any of several wireline tools, including the formation evaluation tool 120 described above and shown in FIG. 1. In other embodiments, the downhole spectrometer may be incorporated into a while-drilling tool, such as the tool 120 or BHA 220 described above and shown in FIG. 2. The downhole spectrometer 300 may include multiple optical channels with each optical channel sharing one or more light sources. The downhole spectrometer 300 in other non-limiting embodiments may include multiple optical channels with each optical channel having a light source.

In one non-limiting embodiment, the downhole spectrometer 300 may include a single light source 322. In the non-limiting example shown the downhole spectrometer 300 includes an array 302 of individual light sources 322. The light source 322 or array 302 emits light toward a fluid sample cell 304 via an optical path 320. The optical path may be any path that provides optical transmission. In one embodiment, the optical path 320 may include an air gap. In another embodiment, the optical path 320 may include an optical fiber or a plurality of optical fibers.

The fluid sample cell 304 includes at least one window 306 for receiving the emitted light, so that the light may interact with fluid 308 within the fluid sample cell 304. Several configurations of fluid sample cells and windows may be used in other embodiments without departing from the scope of the present disclosure. For example, to measure optical transmittance through a fluid sample cell, one could use a pair of windows. Transflectance measurements may be conducted using a single window with a mirror in the fluid sample cell behind the window and having the fluid sample between the mirror and window. Attenuated reflectance measurements may be conducted using a single window in contact with the fluid sample. Raman scattering and fluorescence measurements may be conducted using a single window and collecting the resulting light on the same side of the window as the source light. In another example, light may be collected through a second window for Raman scattering and fluorescence measurements. Depending on the opacity of the fluid sample, the second window may collect the resulting light at 90 degrees from the direction of the source light.

Continuing with the example of FIG. 3, at least one photodetector 310 receives at least a portion of the light after the light interacts with the fluid 308. The photodetector 310, which may be a single broadband photodetector, is responsive to light emitted from the light source 322 or array 302 and provides an output signal indicative of the light received at the photodetector 310. In some cases, the photodetector output signal is an analog electrical signal. An analog-to-digital converter 312 may be used to convert the photodetector output signal into a digital signal that is received by a processor that is part of a controller 314, 316. The light emitted from the light source 322 or array 302 may be modulated by a processor 142 within the same controller 314 that receives the photodetector output or by a separate modulator in a second controller 316. In the example shown, one controller 314 is coupled to the photodetector 310 and a second controller 316 is coupled to the array 302 for modulating light emitted by the light source 322 or the array 302. These controllers may be implemented as a single controller without departing from the scope of the disclosure. In other embodiments, the controller or controllers 314, 316 may be located at the surface of the well borehole.

In wireline embodiments, communication may be accomplished via the wireline cable. In while-drilling embodiments, communication may be accomplished via wired pipe, acoustic pipe communication, or by mud-pulse telemetry. In wireline embodiments disclosed herein, the light source 322 or array 302 may be located at a well borehole surface location and the light path 320 may include one or more optical fibers extending from the surface location to the downhole tool using the wireline cable as a support. In this surface light source 322 or array 302 embodiment, spectroscopy operations disclosed herein may be accomplished by controlling the array 302 at the surface.

In one embodiment, the light source 322 or array 302 may include one or more light emitting semiconductors used as the individual light sources 322. For example, the one or more light sources 322 may include one or more quantum cascade lasers, which may include one or more ridge waveguide quantum cascade lasers, one or more buried heterostructure waveguide quantum cascade lasers, one or more Fabry Perot quantum cascade lasers, one or more distributed feedback ("DFB") quantum cascade lasers, one or more distributed Bragg reflector ("DBR") quantum cascade lasers, or any combination thereof. As used herein, "quantum cascade laser" or "QCL," refers generally to quantum cascade lasers, types of which include ridge waveguide quantum cascade lasers, buried heterostructure waveguide quantum cascade lasers, Fabry Perot quantum cascade lasers, DFB quantum cascade lasers and DBR quantum cascade lasers. Quantum cascade lasers exhibit relatively narrow line widths and good wavelength tunability.

The individual light sources 322 may be operated continuously or in a pulsed mode to emit a light of a selected wavelength or wavelengths toward the fluid sample cell 304. In several non-limiting embodiments, the individual light sources can emit light in the infrared region, for example from about 2.5 μm to about 10 μm. The wavelength of DFB quantum cascade lasers may be changed such that the derivative of the spectra may be measured which can remove the requirement for background calibration.

In one non-limiting example, the individual light sources 322 may all be coupled to a single optical fiber 320. The individual light sources 322, as other embodiments, may be coupled to a plurality of optical fibers 320. The individual light sources 322 or groups of two or more individual light sources 322 may be independently coupled to one or more optical fibers 320, where each optical fiber transmits light emitted from a single light source 322 or group of individual light sources 322. At least a portion of the light emitted by the individual light sources 322 may be transmitted through the optical fibers 320 to the fluid sample cell 304. The light may interact, for example, through transmission or through attenuated reflection with the fluid 308 in the fluid sample cell 304. The light may be detected after fluid interaction by the photodetector 310. In other embodiments, the downhole spectrometer 300 may include arrayed light sources 322 that are not all QCL lasers. Non QCL light sources 322 may include optical channels that have a wider bandpass and less resolution than a laser light source. Non-limiting examples of non-QCL light sources include light-emitting diodes (LEDs), laser diodes and broadband light sources.

The light emitted by each light source 322 in the array 302 may be modulated by the associated controller 314, 316, 114. The processor 142 that receives the detector 310 output signal may also receive a signal from the controller 314, 316, 114 modulating the array 302, where the modulator signal is indicative of which individual light source 322 within the array 302 emitted the light at a particular point in time or of a particular frequency or of a particular wavelength or of a particular intensity. When each light source is modulated and/or selected to emit a predetermined wavelength, then no filtering is required for distinguishing spectra over the wide bandwidth of the array 302.

Multiple wavelengths emitted by QCL lasers arranged in an array may be detected using a single photodetector. Photodetectors typically experience drift with respect to another as temperature increases, meaning that the response characteristics of each photodetector is unique when subjected to temperature fluctuations. Using a single photodetector eliminates the need to account for differences in how one photodetector drifts with respect to other photodectors. A common optical measurement is absorbance, which is the base ten logarithm of the ratio of light entering a fluid sample to light exiting the fluid sample. From experience, we found that, although a photodetector's response is diminished at elevated temperatures and its baseline drifts, its response still varies linearly with incident light intensity. Thus, using a single photodetector when making a ratio measurement such as absorbance, especially at high temperatures, avoids errors due to drift. Because of its simplicity, the spectrometer 300 according to the disclosure has a high reliability and is robust.

Each light source 322 in the array 302 can be configured or selected to emit a light having a wavelength corresponding to a different optical channel of the spectrometer 300. In one embodiment, modulating the light sources includes turning each light source on individually and sequentially using the controller 314, 316 so that each light source 322 in the array 302 emits a specific wavelength of light through the fluid cell 304 at a different time. An optical absorption spectrum can then be generated by comparing, for each wavelength, the response when the fluid cell is filled with fluid to the response when the cell is empty.

Cooling downhole components may improve performance. For example, cooling in some cases could improve photodetector signal-to-noise ratio and may increase light source brightness. Cooling one or more downhole components may be accomplished using a cooling device 318. The cooling device 318 used may be any number of devices, examples of which include thermal-electric, thermo-tunneling, sorption cooling, evaporators, and Dewar. Cooling is optional where components selected are compatible with the downhole temperature environment. Cooling may also be applied where a component operating temperature is lower than the downhole environment and/or were cooling may enhance performance of the component. In several embodiments, the light source 322 and/or the array 302 is compatible with the downhole temperature environment. In other embodiments, the light sources 322 and/or the array 302 may be cooled using the cooling device 318.

Maintaining the at least one light source at a constant temperature could provide wavelength stability. In one embodiment, the array is maintained at a substantially constant temperature, and the wavelength of each light source may be modulated by rapidly changing its temperature over a small temperature range. This would most easily be done by rapidly changing the current through the light source or by changing electrical current supplied to auxiliary resistive heaters in thermal contact with each light source. In another embodiment the wavelength is modulated by using an external cavity. Alternatively, each light source's wavelength could be slightly modulated by slightly modulating its temperature, which is done most easily by modulating the current through it.

In another embodiment, the wavelength of each QCL may be modulated at a different frequency, which would save time through the multiplexing advantage associated with measuring all wavelengths simultaneously with a single photodetector. Then, the output of the photodetector could be filtered (digitally or in hardware) to recover that portion of the photodetector response that is due to any particular laser.

Figure 4:
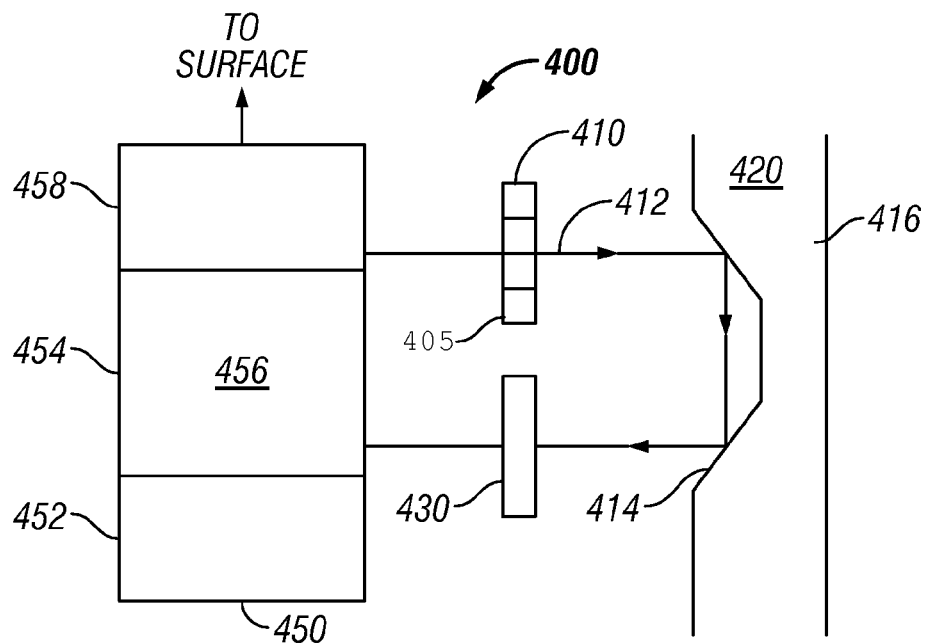
FIGS. 4 and 5 illustrate downhole Raman spectrometer examples according to several embodiments of the disclosure.

Turning now to FIG. 4, a schematic diagram illustrates a Raman spectrometer 400 that may be used downhole for analyzing fluid withdrawn from a formation. The Raman spectrometer 400 includes at least one light source 405 that induces or pumps infrared light 412 via a light path 320 into a fluid 420 through a window 414 made into a wall of a fluid chamber 416. The at least one light source 405 may include one or more QCL lasers as described above and shown in FIG. 3. The exemplary Raman Spectrometer 400, as shown in FIG. 4 includes an array 410 of QCL light sources. The light path 320 from the at least one light source 405 to the window 414 may include at least one optical fiber such as the fiber described above and shown in FIG. 3. The array 410 of this non-limiting example includes multiple light sources producing infrared light, for example mid-infrared light, within a relatively narrow wavelength band. Alternatively, the array 410 may produce multiple monochromatic (single wavelength) infrared light from each light source 405. The infrared light 412 interacts with the fluid 420 and at least a portion of the light is reflected back to a photodetector 430. The photodetector 430 produces a signal responsive to the light, which signal is received by a controller 450 for analysis. The photodetector 430 may be any photodetector that can detect spectra of the Raman scatters corresponding to the light emitted by the at least one light source 405 and/or the array 410. The controller 450 may further be used as a modulator for the at least one light source 405 to modulate the light emitted from the light source 405.

The photodetector signals are passed to the controller 450, which may include a processor 452, and memory for storing data 454 and computer programs 456. The controller 450 receives and processes the signals received from the detector 430. In one aspect, the controller 450 may analyze or estimate the detected light and transmit a spectrum of the Raman scattered light to a surface controller using a transmitter 458. In one aspect, the controller 450 may analyze or estimate one or more properties or characteristics of the fluid downhole and transmit the results of the estimation to a surface controller using the transmitter 458. In another aspect, the controller 450 may process the signals received from the detector 430 to an extent and telemeter the processed data to a surface controller for producing a spectrum and for providing an in-situ estimate of a property of the fluid, including the contamination level of the mud in the formation fluid. The spectrum provided by the Raman spectrometer 400 may be used to evaluate, for example, oil-based mud contamination and relative components in crude oils of one or more compounds in the fluid sample, such as esters or olefins.

Figure 5:
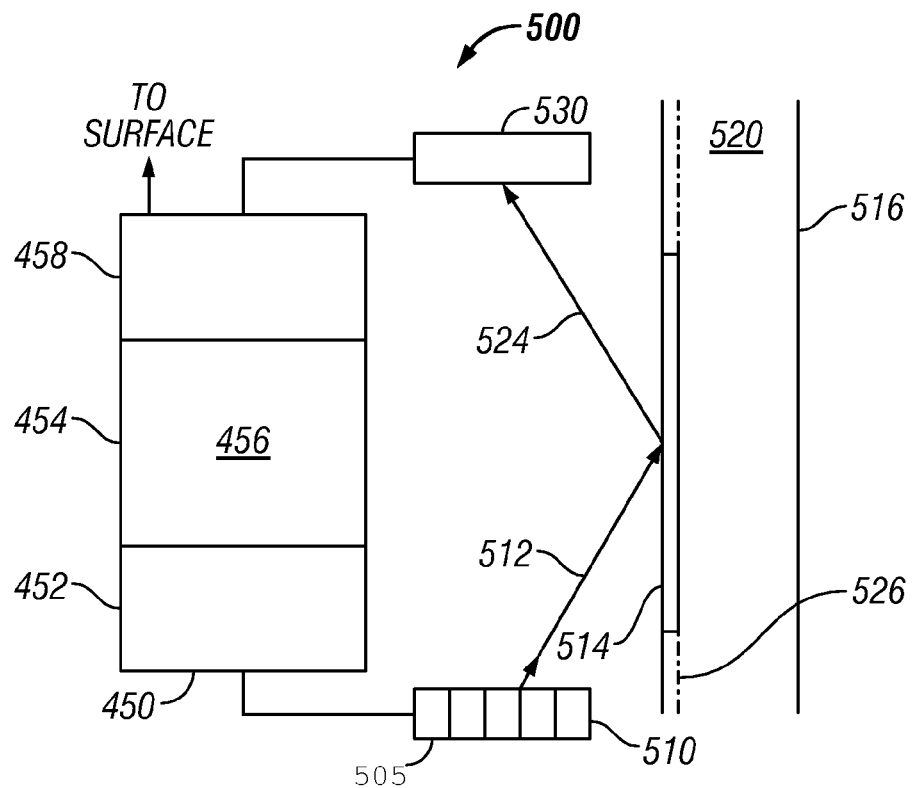

FIG. 5 is a non-limiting schematic diagram showing a portion of a surface-enhanced Raman spectrometer 500 for estimating a property of a fluid according to one embodiment of the disclosure. The exemplary spectrometer 500 shown includes a fluid sample cell 516 for holding a fluid 520 to be analyzed. The fluid 520 may be stationary or it may be flowing through the fluid sample cell 516. The fluid sample cell 516 includes a window 514 for allowing light to pass to the fluid 520. The spectrometer 500 includes at least one QCL 505 that emits light 512. The spectrometer 500 as shown in FIG. 5 includes an array 510 of QCL light sources that emit light 512. Each laser in the array 510 may emit a desired wavelength or band of wavelengths. A controller 450 substantially as described above and shown in FIG. 4 may be used to control the operation of the QCL array 510 to modulate the lasers of the array. The light path from the array 510 to the window 514 may be an optical fiber such as the fiber 320 described above and shown in FIG. 3. The incident light 512 enters the fluid sample cell 516 through the window 514 at a selected angle. The Raman scattered light 524 from the fluid 520 leaves the window 514. A photodetector 530, similar to the photodetector 430 described above and shown in FIG. 4 detects the Raman spectra. A processor 452 receives the signals from the photodetector 530 and processes the signals to estimate a property of the fluid 520. The controller 450 may further include memory 454 and programs 456 for storing information and programs for controlling the tool. Likewise, a transmitter 458 may be used to communicate with surface-located components.

Fluorescence can interfere with the Raman signals, so to increase the intensity of the Raman signal, an inside surface of the chamber 516 including the inside surface of the window 514 may be coated with conductive particles 526. The conductive particles 526 may be placed in the form of scattered metallic particles, a lattice type structure, or in any other suitable form that will enhance the Raman scattered light. The conductive particles can enhance the Raman Effect due to Plasmon resonance, which consists of energy exchange between the Raman signals and a surface wave that exists in a conductive layer, such as the layer of particles 526. The spectrometer 500 may be used downhole for in-situ analysis of a fluid, such as the fluid withdrawn from a formation. In other operational embodiments, the spectrometer 500 may be used at the surface to estimate one or more properties or characteristics of the fluid. The spectrometer 500 may be used to evaluate, for example, oil-based mud contamination and relative components in crude oils of one or more compounds in the fluid sample, such as the presence of esters or olefins.

Referring now to the several non-limiting embodiments described above and shown in FIGS. 1-5, one skilled in the art with the benefit of the present disclosure will better understand several non-limiting operational examples. An optical absorption spectrum can be generated using single-pass and/or multiple-pass absorption spectroscopy to indicate the presence of one or more specified molecules in a fluid sample. Oil-based mud filtrate often has a distinct spectral signature due to the presence of olefins and esters, which do not naturally occur in crude oils. For example, olefins produce peaks in the mid-infrared region from about 800 $cm^{-1}$ to about 1000 $cm^{-1}$ and esters produce peaks from about 1,600 $cm^{-1}$ to about 1,800 $cm^{-1}$. In operation, the downhole spectrometer 300 can be used to estimate the percentage of oil based mud filtrate contamination of crude oil samples as they are being collected downhole. One can continue withdrawing and discarding oil removed from the downhole formation until the contamination falls below a desired level and then divert a clean fluid sample being withdrawn into a sample collection tank.

In one non-limiting example, a method for estimating downhole fluid properties may include using any of the several tool embodiments described above and shown in FIGS. 1 through 5. In one embodiment, a QCL may be used to emit infrared light of a desired wavelength toward a fluid sample cell containing a fluid. The light interacts with the fluid and is detected by a photodetector. An output signal from the photodetector may then be processed using a downhole or surface processor to estimate one or more properties of the fluid in the fluid sample cell. For example, the properties may include identification of particular compounds. In several embodiments, the method may be used to determine whether the fluid sample includes synthetic based oils containing olefins and/or esters or whether the fluid sample is a pristine formation fluid sample.

In some embodiments, a tool such as the spectrometer described above may be used for permanent well monitoring. In these embodiments, the spectrometer or at least a portion of the spectrometer may be installed within a producing well to monitor production fluids. In some cases, producing wells may produce harmful compounds and/or gasses that may cause damage to equipment or present hazards at the well site. In one example, the method includes monitoring a producing well to estimate production fluid properties. The fluid properties may include the presence of harmful compounds such as hydrogen sulfide, carbonyl sulfide, cyanide, hydrogen cyanide, sulfur dioxide, and brine.

In at least one embodiment, one or more spectrometers or at least a portion of the spectrometers, as described and discussed above, may be used to periodically or continuously monitor production fluids. For example, one or more readings can be taken with at least one spectrometer every 30 seconds, minute, two minutes, 5 minutes, one-half hour, hour, two hours, or any periodic interval desired. In another example, at least one spectrometer can continually acquire data which can be processed in real time or stored and, if desired, later analyzed to provide a continuous monitoring of the production fluid as it is acquired.

Having described above the several aspects of the disclosure, one skilled in the art will appreciate several particular embodiments useful in determining a property of an earth subsurface structure using a downhole spectrometer.

In one particular embodiment, an apparatus for estimating a downhole fluid property includes a carrier conveyable into a well borehole with one or more light sources carried by the carrier. The one or more light sources include at least one quantum cascade laser light source. A fluid sample cell receives light emitted from the one or more light sources, and at least one photodetector detects light emitted from the one or more light sources after the light interacts with a fluid in the fluid sample cell.

In another particular embodiment, an apparatus for estimating a downhole fluid property includes at least one quantum cascade laser light source that is a distributed feedback quantum cascade laser. In another particular embodiment, an apparatus for estimating a downhole fluid property includes at least one quantum cascade laser light source that includes at least one of a ridge waveguide quantum cascade laser, a buried heterostructure waveguide quantum cascade laser, a Fabry Perot quantum cascade laser, a distributed feedback quantum cascade laser, and a distributed Bragg reflector quantum cascade laser.

In several particular embodiments, an apparatus for estimating a downhole fluid property includes a modulator that modulates light emitted from at least one quantum cascade laser light source. In one embodiment the modulator modulates a temperature of the at least one quantum cascade laser light source. In another embodiment, the modulator modulates the temperature by changing an electrical current supplied to the at least one quantum cascade laser light source. In other embodiments, the modulator modulates a parameter and the parameter includes one or more of a light intensity, a wavelength, an on-off cycle, a frequency, and a temperature.

In another particular embodiment, an apparatus for estimating a downhole fluid property includes a non-linear optical medium carrying light emitted from the at least one quantum cascade laser light source to the fluid sample cell. In another particular embodiment the apparatus for estimating a downhole fluid property includes one or more light sources that include at least one of a distributed feedback quantum cascade laser, a light emitting diode, a laser diode, and a broadband light.

In one particular embodiment, an apparatus for estimating a downhole fluid property includes a plurality of quantum cascade laser light sources. In a particular embodiment, the apparatus for estimating a downhole fluid property includes a plurality of quantum cascade laser light sources that emit at least two wavelengths of light.

In one embodiment an apparatus for estimating a downhole fluid property has a photodetector that comprises a single photodetector having a response band at least as wide as an emitted bandwidth from the one or more light sources.

In a particular embodiment, a method for estimating a downhole fluid property includes conveying one or more light sources into a well borehole using a carrier, the one or more light sources comprising at least one quantum cascade laser light source, emitting light from the at least one quantum cascade laser light source toward a fluid sample cell containing a downhole fluid, and detecting the light emitted from the at least one quantum cascade laser light source after the light interacts with the downhole fluid in the fluid sample cell using at least one photodetector.

In another particular embodiment, a method for estimating a downhole fluid property includes at least one quantum cascade laser light source that is a distributed feedback quantum cascade laser.

In several particular embodiments, a method for estimating a downhole fluid property includes modulating the light emitted from the at least one quantum cascade laser light source. Modulating the light may include modulating a temperature, a light intensity, a wavelength, a frequency, an on-off cycle, or any combination thereof of the at least one quantum cascade laser.

In one embodiment, a method for estimating a downhole fluid property includes at least one quantum cascade laser light source that includes a plurality of quantum cascade laser light sources. In another embodiment, the method includes emitting light at a plurality of narrow wavelengths, wherein each quantum cascade laser light source emits a unique wavelength of light.

In one embodiment, a method for estimating a downhole fluid property includes receiving light at a photodetector using a single photodetector having a response band at least as wide as an emitted bandwidth from the at least one quantum cascade laser. In another embodiment the method includes emitting light from a first quantum cascade laser and a second quantum cascade laser and passing the emitted light through a non-linear optical medium to the fluid sample cell.

In several particular embodiments, a method for estimating a downhole fluid property includes esters, olefins, or both and the method further includes estimating the fluid property using the light detected by the at least one photodetector. The fluid property may include evaluating the level of oil based mud contamination in a crude oil.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

Given the above disclosure of general concepts and specific embodiments, the scope of protection is defined by the claims appended hereto. The issued claims are not to be taken as limiting Applicant's right to claim disclosed, but not yet literally claimed subject matter by way of one or more further applications including those filed pursuant to the laws of the United States and/or international treaty.

What is claimed is:

1. An apparatus for estimating a downhole fluid property, the apparatus comprising:
a carrier conveyable into a well borehole;
an array of quantum cascade lasers carried by the carrier;
a modulator configured to apply a substantially constant temperature to the array, the modulator configured to modulate at least one of a frequency of emitted light, a wavelength of the emitted light, an intensity of the emitted light and a temperature of at least one quantum cascade laser of the array of quantum cascade lasers in a downhole environment;
a fluid sample cell that receives light emitted from the one or more light sources; and
at least one photodetector configured to be operated in a downhole environment, that detects light emitted from the one or more light sources after the light interacts with a fluid in the fluid sample cell.

2. An apparatus according to claim 1, wherein the array of quantum cascade laser light sources includes one or more of a ridge waveguide quantum cascade laser, a buried heterostructure waveguide quantum cascade laser, a Fabry Perot quantum cascade laser, a distributed feedback quantum cascade laser, and a distributed Bragg reflector quantum cascade laser.

3. An apparatus according to claim 1, wherein the modulator is configured to modulate an on-off cycle of the at least one quantum cascade laser.

4. An apparatus according to claim 1 further comprising a non-linear optical medium carrying light emitted from the at least one quantum cascade laser light source to the fluid sample cell.

5. An apparatus according to claim 1, wherein the array of quantum cascade lasers comprises a plurality of quantum cascade laser light sources, the plurality of quantum cascade laser light sources emitting at least two wavelengths of light.

6. An apparatus according to claim 1, wherein the photo detector comprises a single photodetector having a response band at least as wide as an emitted bandwidth from the array of quantum cascade lasers.

7. A method for estimating a downhole fluid property comprising:
conveying an array of quantum cascade lasers into a well borehole using a carrier, the array of quantum cascade lasers comprising at least one quantum cascade laser having a parameter configured to be modulated in a downhole environment, the parameter including at least one of a frequency of emitted light, a wavelength of the emitted light, an intensity of the emitted light and a temperature of the at least one quantum cascade laser;
applying a substantially constant temperature to the array of quantum cascade lasers;
emitting light from the at least one quantum cascade laser toward a fluid sample cell containing a downhole fluid; and
detecting the light emitted from the at least one quantum cascade laser after the light interacts with the downhole fluid in the fluid sample cell using at least one photodetector configured to be operated in a downhole environment, the fluid property being estimated at least in part by using the light detected by the at least one photodetector.

8. A method according to claim 7, wherein the array of quantum cascade lasers comprises one or more of a ridge waveguide quantum cascade laser, a buried heterostructure quantum cascade laser, a Fabry Perot quantum cascade laser, a distributed feedback quantum cascade laser, and a distributed Bragg reflector quantum cascade laser.

9. A method according to claim 7, wherein the parameter further includes an on-off cycle of the at least one quantum cascade laser.

10. A method according to claim 7, wherein the array of quantum cascade lasers comprises a plurality of quantum cascade laser light sources and wherein emitting the light comprises emitting light at a plurality of narrow wavelengths, wherein each quantum cascade laser light source emits a unique wavelength of light.

11. A method according to claim 7, wherein detecting the light comprises using a single photodetector having a response band at least as wide as an emitted bandwidth from the array of quantum cascade lasers.

12. A method according to claim 7, wherein emitting light comprises emitting light from a first quantum cascade laser and a second quantum cascade laser, the method further comprising passing the emitted light through a non-linear optical medium to the fluid sample cell.

13. A method according to claim 7, wherein the fluid property comprises esters, olefins, or both.

14. A method according to claim 7, wherein estimating the fluid property comprises evaluating the level of oil based mud contamination in a crude oil.

15. A method for monitoring a production well comprising:
disposing an array of quantum cascade lasers into a wellbore and in fluid communication with a production well product line, the array of quantum cascade lasers comprising at least one quantum cascade laser having a parameter configured to be modulated in a downhole environment, the parameter including at least one of a frequency of emitted light, a wavelength of the emitted light, an intensity of the emitted light and a temperature of the at least one quantum cascade laser;
applying a substantially constant temperature to the array of quantum cascade lasers;
emitting light from the at least one quantum cascade laser toward a fluid sample cell containing a production fluid; and
detecting the light emitted from the at least one quantum cascade laser light source after the light interacts with the production fluid in the fluid sample cell using at least one photodetector configured to be operated in a downhole environment.

16. A method according to claim 15 further comprising monitoring the production fluid for one or more contaminants.

17. A method of claim 16, wherein the one or more contaminants comprise at least one of hydrogen sulfide, carbonyl sulfide, cyanide, hydrogen cyanide, sulfur dioxide, and brine.

* * * * *